United States Patent [19]

Hackler et al.

[11] Patent Number: 5,597,836
[45] Date of Patent: Jan. 28, 1997

[54] N-(4-PYRIDYL) (SUBSTITUTED PHENYL) ACETAMIDE PESTICIDES

[75] Inventors: Ronald E. Hackler; Peter L. Johnson, both of Indianapolis, Ind.

[73] Assignee: DowElanco, Indianapolis, Ind.

[21] Appl. No.: 385,029

[22] Filed: Feb. 7, 1995

Related U.S. Application Data

[60] Division of Ser. No. 932,405, Aug. 19, 1992, Pat. No. 5,399,564, which is a continuation-in-part of Ser. No. 753,519, Sep. 3, 1991, abandoned.

[51] Int. Cl.$^6$ .................. C07D 213/72; C07D 213/75; C07D 213/81; A01N 43/40
[52] U.S. Cl. .................. 514/352; 546/264; 546/285; 546/268.1; 546/296; 546/304; 546/309
[58] Field of Search .................. 546/297, 309; 514/313, 352

[56] References Cited

U.S. PATENT DOCUMENTS

| | | | |
|---|---|---|---|
| 3,983,107 | 9/1976 | Holland | 260/240 |
| 5,114,939 | 5/1992 | Dreikorn et al. | 514/248 |
| 5,145,843 | 9/1992 | Arnold et al. | 514/63 |

FOREIGN PATENT DOCUMENTS

| | | | |
|---|---|---|---|
| 0410762A1 | 1/1991 | European Pat. Off. | 546/122 |
| 1141707 | 1/1969 | United Kingdom . | |
| 2052481 | 1/1981 | United Kingdom | 546/153 |
| 90/02736 | 3/1990 | WIPO . | |

OTHER PUBLICATIONS

H. Pines, et al. "Base–Catalyzed Reactions XXXIV," *J. Org. Chem*, vol. 34, pp. 2113–2118 (Jul. 1969).
Derwent Abstract 30248–C, abstracting JA 7116106 (1971).
K. C. Crook, "Preparation of 2- and 4-Benzypyridine," *J.A.C.S.*, vol. 70, pp. 416–417 (1948).
Hideo Takeshiba, et al., "Benzylpyridine," *Ann. Sankyo Res. Lab.*, vol. 23, pp. 225–232 (1971).
Derwent Abstract 86–121849/19, abstracting JP 61060651A (1986).
CA Selects: Insecticides, Issue 23 (1988), abstract No. 109:165735a, abstracting JP 6333305.
CA Selects: Novel Pesticides & Herbicides, Issue 19 (1989), p. 6, abst. no. 111:77855a, abstracting EP 302,366.
CA Selects: Novel Pesticides & Herbicides, Issue 19 (1989), p. 7, abst. No. 111:77856b, abstracting EP 302,365.
Chemical Abstracts, vol. 113,, pp. 633–634, abst 113:132010q, abstracting PCT appln WO 90 02,736 (1990).
Derwent Abstracts 90–115943/15, abstracting PCT appln WO 90 02,736 (1990).
P. C. Jain et al., "107 –Substituted Alkylamino–3–aminopyridines," *J. Med. Chem.*, vol. 14, pp. 87–89 (1968).
P. C. Jain et al., Journal of Medicinal Chemistry, vol. 14, pp. 87–89 (1968).

*Primary Examiner*—Alan L. Rotman
*Attorney, Agent, or Firm*—Donald R. Stuart

[57] ABSTRACT

N-(4-Pyridyl) arylacetamides, for example N-((3-chloro-2-ethyl)-4-pyridyl)(4-(4-chlorophenoxy)phenyl)-acetamide, and 4-(aralkyoxy or aralkylamino)pyridines, for example 4-[2-[4-(2,2,2-trifluoroethoxy)phenyl]ethoxy]pyridine, are active against nematodes, insects, mites, and plant pathogens.

12 Claims, No Drawings

N-(4-PYRIDYL) (SUBSTITUTED PHENYL) ACETAMIDE PESTICIDES

RELATED APPLICATIONS

This application is a division of Ser. No. 07/932 405 filed Aug. 19, 1992, U.S. Pat. No. 5,399,564, which is a continuation-in-part of Ser. No. 07/753,519, filed Sep. 3, 1991, abandoned.

FIELD OF THE INVENTION

This invention provides new compounds that are useful as nematicides, insecticides, miticides, and plant fungicides. The invention also provides nematicidal, insecticidal, miticidal, and fungicidal methods.

There is an acute need for new nematicides, insecticides, miticides, and plant fungicides. Available nematicides typically have high mammalian toxicity and must be used at high rates. A nematicide that can be applied at lower rates and that has lower mammalian toxicity would represent a significant advance.

Mites and insects are developing resistance to the miticides and insecticides in current use. Resistance to insecticides in anthropods is widespread, with at least 400 species resistant to one or more insecticides. The development of resistance to some of the older insecticides, such as DDT, the carbamates, and the organophosphates is well known. But resistance has even developed to some of the newer pyrethroid insecticides and miticides. Similarly, target pathogens are rapidly developing resistance to currently used fungicides. At least 50 species of fungi have developed resistance to the benzimidazole fungicides. Even recently introduced fungicides, like the acylalanines, which initially exhibited excellent control of potato late blight and grape downy mildew in the field, have become less effective because of resistance. Therefore a need exists for new insecticides, miticides, and fungicides, and particularly for compounds that have new or atypical modes of action.

SUMMARY OF THE INVENTION

This invention provides compounds of the formula (1):

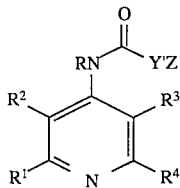

(1)

and N-oxides and salts thereof, wherein

R is H, $(C_1-C_4)$alkyl, or benzyl;

$R^1$, $R^2$, $R^3$, and $R^4$ are one of the following:
  a) $R^3$ and $R^4$ are H, and $R^1$ and $R^2$ are independently halo, $(C_1-C_4)$ alkyl, halo $(C_1-C_4)$ alkyl, $(C_3-C_4)$ branched alkyl, $(C_3-C_7)$cycloalkyl, $(C_1-C_4)$alkoxy, or halo$(C_1-C_4)$alkoxy;
  b) one of $R^1$, $R^2$, $R^3$, and $R^4$ is $(C_1-C_4)$ alkyl, $(C_3-C_4)$ branched alkyl, $(C_1-C_4)$ alkoxy, halo $(C_1-C_4)$ alkyl, halo $(C_1-C_4)$ alkoxy, $(C_1-C_4)$ alkylthio, $(C_1-C_4)$ alkylsulfinyl, $(C_1-C_4)$ alkylsulfonyl, aryl, or substituted amino, and the rest are H;
  c) $R^1$, $R^2$, $R^3$, and $R^4$ are independently H or halo; or
  d) $R^1$ and $R^2$ combine to form a $(C_5-C_6)$ saturated or unsaturated carbocyclic ring that is optionally substituted with one or two groups selected from halo, $(C_1-C_4)$alkyl, $(C_3-C_4)$ branched alkyl, halo$(C_1-C_4)$alkyl, $(C_3-C_7)$cycloalkyl, $(C_1C_4)$alkoxy, halo$(C_1-C_4)$alkoxy, or $NO_2$, and $R^3$ and $R^4$ are H;

$R^5$ is H, $(C_1-C_4)$ alkyl or $(C_1-C_4)$ acyl;

$R^6$ and $R^7$ are independently $(C_1-C_4)$ alkyl, $(C_3-C_4)$ branched alkyl, phenyl, or substituted phenyl;

Y'Z together form a $C_4-C_{11}$ saturated or unsaturated hydrocarbon chain, straight chain or branched, optionally including a hetero atom selected from O, $NR^5$, S, SO, $SO_2$, or $SiR^6R^7$, where $R^5$, $R^6$, and $R^7$ are as defined above, and optionally substituted with one or more groups independently selected from $(C_1-C_4)$ alkyl, $(C_2-C_4)$ alkenyl, $(C_2-C_4)$ alkynyl, branched $(C_3-C_7)$ alkyl, $(C_3-C_7)$ cycloalkyl, $(C_3-C_7)$cycloalkenyl, halo, halo $(C_1-C_4)$alkyl, halo $(C_1-C_4)$ alkoxy, hydroxy, or $(C_1-C_4)$ acyl; or Y' is bond or a bivalent hydrocarbon radical one to five carbon atoms long, optionally substituted with $(C_1-C_4)$ alkyl, $(C_2-C_4)$alkenyl $(C_2-C_4)$alkynyl, branched $(C_3-C_7)$ alkyl, $(C_3-C_7)$ cycloalkyl or $(C_3-C_7)$ cycloalkenyl, halo, halo $(C_1-C_4)$ alkyl, halo $(C_1-C_4)$ alkoxy, hydroxy, CN, or $(C_1-C_4)$ acyl; and Z is
  (a) aryl or
  (b) $(C_3-C_8)$ cycloalkyl or cycloalkenyl, optionally substituted with one or more groups independently selected from $(C_1-C_4)$alkyl, $(C_1-C_4)$ alkoxy, halo $(C_1-C_4)$ alkyl, halo $(C_1-C_4)$ alkoxy, halo, hydroxy, or $(C_1-C_4)$ acyl; where aryl is
  (a) a phenyl group optionally substituted with one or more groups independently selected from:
  halo,
  I,
  $(C_3-C_8)$ cycloalkyl,
  $(C_3-C_8)$ cycloalkenyl,
  phenoxy,
  substituted phenoxy,
  phenylthio,
  substituted phenylthio,
  phenyl
  substituted phenyl,
  $NO_2$,

where $R^8$ is $(C_1-C_7)$ alkyl, halo $(C_1-C_7)$ alkyl, $(C_3-C_7)$ branched alkyl, halo $(C_3-C_7)$ branched alkyl, $(C_3-C_7)$ cycloalkyl, halo $(C_3-C_7)$ cycloalkyl, $(C_1-C_7)$ alkoxy, phenyl, or substituted phenyl,
  acetoxy,
  OH,
  CN,
  $SiR^9R^{10}R^{11}$ or $OSiR^9R^{10}R^{11}$, where $R^9$, $R^{10}$ and $R^{11}$ are independently $(C_1-C_4)$ alkyl, $(C_3-C_4)$ branched alkyl, phenyl, or substituted phenyl,
  $NR^{12}R^{13}$, where $R^{12}$ and $R^{13}$ are independently H, $(C_1-C_4)$ alkyl, or $(C_1-C_4)$ acyl,
  $S(O) R^{14}$, or $SO_2^{R14}$, where $R^{14}$ is $(C_1-C_{10})$ alkyl, phenyl, or substituted phenyl;

a $C_1-C_{12}$ saturated or unsaturated hydrocarbon chain, straight chain or branched optionally including a hetero atom selected from O, S, SO, $SO_2$, $NR^5$, or $SiR^6R^7$, where $R^5$, $R^5$ and $R^7$ are as defined above, and optionally substituted with halo, halo $(C_1-C_4)$ alkoxy, hydroxy, $(C_3-C_8)$ cycloalkyl or cycloalkenyl, $(C_1-C_4)$ acyl, phenoxy, substituted phenoxy, phenyl, substituted phenyl, phenylthio, or substituted phenylthio;

$(C_1-C_7)$ alkoxy optionally substituted with halo, phenyl, substituted phenyl, $(C_3-C_8)$ cycloalkyl or cycloalkenyl, phenoxy, or substituted phenoxy;

$(C_1-C_7)$ alkylthio optionally substituted with halo, phenyl, substituted phenyl, $(C_3-C_8)$ cycloalkyl or cycloalkenyl, phenoxy or substituted phenoxy;

(b) a furyl group of formula (3)

(3)

where $R^{15}$ is H, halo, halomethyl, CN, $NO_2$, $(C_1-C_4)$ alkyl, $(C_3-C_4)$ branched alkyl, phenyl, $(C_1-C_4)$ alkoxy, halo $(C_1-C_4)$ alkoxy;

(c) a thienyl group of the formula (4)

(4)

where $R^{16}$ is H, halo, halomethyl, CN, $NO_2$, $(C_1-C_4)$ alkyl, $(C_3-C_4)$ branched alkyl, phenyl, $(C_1-C_4)$ alkoxy, halo$(C_1-C_4)$ alkoxy or thienyl;

(d) a group of formula (5) or (6)

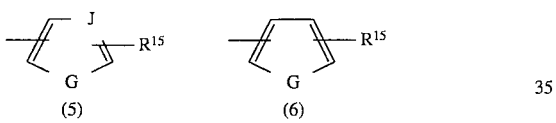

(5)        (6)

where $R^{15}$ as defined in paragraph (b), J is N or CH, and G is O, $NR^{17}$, or S, provided that if J is not N then G is NR, where $R^{17}$ is H, $(C_1-C_4)$ alkyl, $(C_1-C_4)$ acyl, phenylsulfonyl or substituted phenylsulfonyl; p2 (e) a group selected form optionally substituted naphthyl, dihydronaphthyl, tetrahydronaphthyl, and decahydronaphthyl;
optionally substituted indolyl;
1,3-bensodioxolyl;
2,6-dimethyl-4-morpholinyl; and
1-adamantyl;

(f) a group of the formula

wherein m is 4; $R^{20}$ are independently H, halo, lower alkyl, lower alkoxy, haloalkyl, haloalkoxy, $NO_2$, CN, lower alkyl carbonyl, phenoxy, or substituted phenoxy, provided that at least two of $R^{20}$ are selected from H and F; and Het is pyridyl, pyrazinyl, pyrimidinyl, or pyridazinyl, optionally substituted with one or more groups selected form halo, lower alkyl, lower alkoxy, haloalkyl, haloalkoxy, $NO_2$, CN, and lower alkyl carbonyl;

(g) a group of the formula

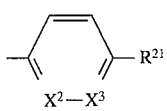

one of $X^2$ and $X^3$ is N and the other is CH;

$R^{21}$ is $-Z-R^{22}$, phenyl, or substituted phenyl;

Z is O or S; and $R^{22}$ is $(C_1-C_4)$ alkyl, $(C_3-C_7)$ branched alkyl, halo $(C_1-C_7)$ alkyl, halo $(C_3-C_7)$ branched alkyl, $(C_1-C_4)$ alkoxy substituted $(C_1-C_4)$ alkyl, or naphthyl or phenyl, either of which may optionally be substituted with up to three groups selected from halo, $(C_1-C_{10})$ alkyl, branched $(C_3-C_7)$ alkyl, halo $(C_1-C_7)$ alkyl, hydroxy $(C_1-C_7)$ alkyl, $(C_1-C_4)$ alkoxy, halo $(C_1-C_4)$ alkoxy, phenoxy, substituted phenoxy, phenyl, substituted phenyl, CN, $NO_2$, OH, $(C_1-C_4)$alkanoyloxy, or benzyloxy.

The invention also provides new compounds of the formula (1A):

(1A)

and N-oxides and salts thereof, wherein $R^1$, $R^2$, $R^3$, and $R^4$ are one of the following:
a) $R^3$ and $R^4$ are H, and $R^1$ and $R^2$ are independently halo, $(C_1-C_4)$ alkyl, halo $(C_1-C_4)$ alkyl, $(C_3-C_4)$ branched alkyl, $(C_3-C_7)$cycloalkyl, $(C_1-C_4)$ alkoxy, or halo $(C_1-C_4)$alkoxy;
b) one of $R^1$, $R^2$, $R^3$, and $R^4$ is $(C_1-C_4)$ alkyl, $(C_3-C_4)$ branched alkyl, $(C_1-C_4)$ alkoxy, halo $(C_1-C_4)$ alkyl, halo $(C_1-C_4)$ alkoxy, $(C_1-C_4)$ alkylthio, $(C_1-C_4)$ alkylsulfinyl, $(C_1-C_4)$ alkylsulfonyl, aryl, or substituted amino, and the rest are H; or
c) $R^1$, $R^2$, $R^3$, and $R^4$ are independently halo or H;

X is O, S, or $NR^5$;

$R^5$ is H, $(C_1-C_4)$ alkyl or $(C_1-C_4)$ acyl;

$R^6$ and $R^7$ are independently $(C_1-C_4)$ alkyl, $(C_3-C_4)$ branched alkyl, phenyl, or substituted phenyl;

YZ together form a $C_5-C_{12}$ saturated or unsaturated hydrocarbon chain, straight chain or branched, optionally including a hetero atom selected from O, $NR^5$, S, SO, $SO_2$, or $SiR^6R^7$, where $R^5$, $R^6$, and $R^7$ are as defined above, and optionally substituted with one or more groups independently selected from $(C_1-C_4)$ alkyl, $(C_2-C_4)$alkenyl, $(C_2-C_4)$alkynyl, branched $(C_3-C_7)$ alkyl, $(C_3-C_7)$ cycloalkyl, $(C_3-C_7)$cycloalkenyl, halo, halo $(C_1-C_4)$ alkyl, halo $(C_1-C_4)$ alkoxy, hydroxy, or $(C_1-C_4)$ acyl; or Y is a bond or a bivalent hydrocarbon radical one to six carbon atoms long, optionally substituted with one or more groups independently selected from $(C_1-C_4)$ alkyl, $(C_2-C_4)$alkenyl or $(C_3-C_7)$alkynyl, branched $(C_3-C_7)$ alkyl, $(C_3-C_7)$ cycloalkyl $(C_3-C_7)$ cycloalkenyl, halo, halo $(C_1-C_4)$ alkyl, halo $(C_1-C_4)$ alkoxy, hydroxy, or $(C_1-C_4)$ acyl; and Z is
(a) aryl or
(b) $(C_3-C_8)$ cycloalkyl or cycloalkenyl, optionally substituted with one or more groups independently selected from $(C_1-C_4)$ alkyl, $(C_1-C_4)$ alkoxy, halo ($C_1$–$C_4$) alkyl, halo ($C_1$–$C_4$) alkoxy, halo, hydroxy, or ($C_1$–$C_4$) acyl; where aryl is
(a) a phenyl group optionally substituted with one or more groups independently selected from:
halo,
I,
($C_3$–$C_8$) cycloalkyl,
($C_3$–$C_8$) cycloalkenyl,
phenoxy,
substituted phenoxy,
phenylthio,
substituted phenylthio,
phenyl,
substituted phenyl,

where $R^8$ is ($C_1$–$C_7$) alkyl, halo ($C_1$–$C_7$) alkyl, ($C_3$–$C_7$) branched alkyl, halo ($C_3$–$C_7$) branched alkyl, ($C_3$–$C_7$) cycloalkyl, halo ($C_3$–$C_7$) cycloalkyl, ($C_1$–$C_7$) alkoxy, phenyl, or substituted phenyl,
acetoxy,
OH,
CN,
$SiR^9R^{10}R^{11}$ or $OSiR^9R^{10}R^{11}$, where $R^9$, $R^{10}$ and $R^{11}$ are independently ($C_1$–$C_4$) alkyl, ($C_3$–$C_4$) branched alkyl, phenyl, or substituted phenyl,
$NR^{12}R^{13}$, where $R^{12}$ and $R^{13}$ are independently H, ($C_1$–$C_4$) alkyl, or ($C_1$–$C_4$) acyl,
$S(O)R^{14}$, or $SO_2R^{14}$, where $R^{14}$ is ($C_1$–$C_{10}$) alkyl, phenyl, or substituted phenyl;

a $C_1$–$C_{12}$ saturated or unsaturated hydrocarbon chain, straight chain or branched optionally including a hetero atom selected from O, S, SO, $SO_2$, $NR^5$, or $SiR^6R^7$, where $R^5$, $R^6$ and $R^7$ are as defined above, and optionally substituted with halo, halo ($C_1$–$C_4$) alkoxy, hydroxy, ($C_3$–$C_8$) cycloalkyl or cycloalkenyl, ($C_1$–$C_4$) acyl, phenoxy, substituted phenoxy, phenyl, substituted phenyl, phenylthio, or substituted phenylthio;

($C_1$–$C_7$) alkoxy optionally substituted with halo, phenyl, substituted phenyl, ($C_3$–$C_8$) cycloalkyl or cycloalkenyl, phenoxy, or substituted phenoxy; or ($C_1$–$C_7$) alkylthio optionally substituted with halo, phenyl, substituted phenyl, ($C_3$–$C_8$) cycloalkyl or cycloalkenyl, phenoxy or substituted phenoxy;

(b) a furyl group of formula (3)

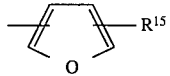  (3)

where $R^{15}$ is H, halo, halomethyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy;

(c) a thienyl group of the formula (4)

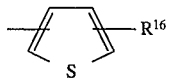  (4)

where $R^{16}$ is H, halo, halomethyl, CN, $NO_2$, ($C_1$–$C_4$) alkyl, ($C_3$–$C_4$) branched alkyl, phenyl, ($C_1$–$C_4$) alkoxy, halo ($C_1$–$C_4$) alkoxy, or thienyl;

(d) a group of formula (5) or (6)

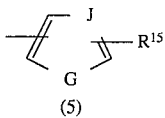 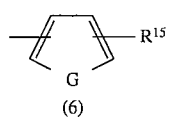

(5)  (6)

where $R^{15}$ is as defined in paragraph (b), J is N or CH, and G is O, $NR^{17}$, or S, provided that if J is not N then G is NR, where $R^{17}$ is H, ($C_1$–$C_4$) alkyl, ($C_1$–$C_4$) acyl, phenylsulfonyl, or substituted phenylsulfonyl;

(e) a group selected from
optionally substituted naphthyl, dihydronaphthyl, tetrahydronaphthyl, and decahydronaphthyl;
optionally substituted pyridyl;
optionally substituted indolyl;
1,3-benzodioxolyl;
2,6-dimethyl-4-morpholinyl; and
1-adamantyl.

The invention also provides a method of inhibiting a nematode population which comprises applying to the locus of a nematode, a nematode inactivating amount of a compound of the formula (1) or (1A) as defined above.

The invention also provides a method of inhibiting an insect or mite population which comprises applying to the locus of the insect or arachnid an effective insect or mime inactivating amount of a compound of formula (1) or (1A).

The invention also provides a method of inhibiting plant pathogens which comprises applying an effective amount of a compound of formula (1) or (1A) to a locus of the pathogen.

DETAILED DESCRIPTION OF THE INVENTION

Throughout this document, all temperatures are given in degrees Celcius, and all percentages are weight percentages unless otherwise stated.

The term "halo" refers to a F, Cl, or Br atom.

The terms "alkoxy", "haloalkyl", "alkylsulfinyl", and "alkylsulfonyl" refer to straight chain and branched chain groups.

The terms "substituted phenyl", "substituted phenoxy", "substituted phenylthio", and "substituted phenylsulfonyl", refer to such groups wherein the phenyl ring is substituted with up to three groups independently selected from halo, I, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, substituted phenoxy, phenyl, substituted phenyl, $NO_2$, OH, CN, ($C_1$–$C_4$)alkanoyl, benzoyl, ($C_1$–$C_4$)alkanoyloxy, ($C_1$–$C_4$) alkoxycarbonyl, phenoxycarbonyl, or benzoyloxy.

The terms "substituted naphthyl", and "substituted indolyl" refer to these ring systems substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "carbocyclic ring" refers to a saturated or unsaturated carbocyclic ring containing five or six carbon atoms.

The term "unsaturated hydrocarbon chain" refers to a hydrocarbon chain containing one or more sites of unsaturation.

The term "HPLC" refers to a high pressure liquid chromatography.

The term "bivalent hydrocarbon radical" refers to bivalent radicals derived from normal alkanes by removal of hydrogen atoms from each of the two terminal carbon atoms of the chain, e.g. methylene, ethylene, trimethylene, tetramethylene, etc.

The term "substituted amino" refers to an amino group that is substituted with one or two ($C_1$–$C_4$) alkyl groups or one ($C_1$–$C_4$)alkanoyl group.

The term "lower alkyl" refers to C1 to C6 straight hydrocarbon chains and C3 to C6 branched and cyclic hydrocarbon groups.

The terms "lower alkenyl" and "lower alkynyl" refer to C2 to C6 straight hydrocarbon chains and C3 to C6 branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

Unless otherwise indicated, when it is stated that a group may be substituted with one or more substituents selected from an identified class, it is intended that the substituents may be independently selected from the class.

PREFERRED EMBODIMENTS

Preferred compounds of formulas (1) and (1A) include the following classes:

a) compounds of formulas (1) wherein Y is —$CH_2$— and compounds of formula (1A) wherein Y' is —$CH_2CH_2$—;

b) compounds of formulas (1) and (1A) wherein Z is phenyl;

c) compounds of formulas (1) and (1A) wherein Z is a substituted phenyl group as defined in paragraph (a) of the foregoing definition of "aryl;"

d) compounds of formulas (1) and (1A) wherein Z is a phenyl group substituted with a ($C_2$–$C_4$) alkoxy group;

e) compounds of formulas (1) and (1A) wherein Z is a phenyl group substituted with a ($C_3$–$C_7$)branched alkoxy group;

f) compounds of formulas (1) and (1A) wherein Z is a phenyl group substituted with a halo ($C_2$–$C_4$) alkoxy group;

g) compounds of formulas (1) and (1A) wherein Z is a phenyl group substituted with a halo ($C_3$–$C_7$)branched alkoxy group;

h) compounds of formulas (1) and (1A) wherein Z is a phenyl group substituted with a phenoxy or substituted phenoxy group;

i) compounds of any of the foregoing groups c) to h) wherein the phenyl group is monosubstituted in the 4-position;

j) compounds of formulas (1) and (1A) wherein $R^1$ is ($C_1$–$C_4$) alkyl and $R^2$ is halo;

l) compounds of formulas (1) and (1A) wherein $R^1$ is ethyl and $R^2$ is chloro;

m) compounds of formula (1) wherein $R^1$ and $R^2$ combine to form

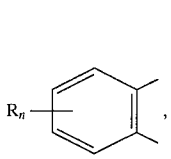

i.e. compounds of the formula (12):

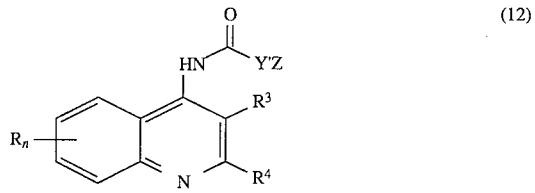

where Y' and Z are as defined above for formula (1), n is 1 or 2, R are independently selected from halo, ($C_1$–$C_4$) alkyl, ($C_3$–$C_4$) branched alkyl, halo ($C_1$–$C_4$) alkyl, ($C_3$–$C_7$)cycloalkyl, ($C_1$–$C_4$) alkoxy, halo ($C_1$–$C_4$) alkoxy, or $NO_2$, and $R^3$ and $R^4$ are H;

n) compounds as defined in foregoing paragraph m) wherein n is 0 or n is 1 and R is 8-fluoro.

o) compounds of formulas (1) and (1A) wherein Z is a group of the formula

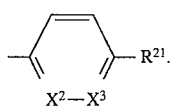

SYNTHESIS

The compounds of this invention are made using well known chemical procedures. The required starting materials are commercially available, or they are readily synthesized using standard procedures.

Compounds of Formula (1) can be prepared using the process illustrated in the following scheme:

Scheme 1

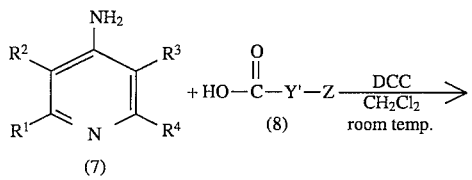

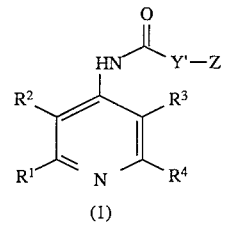

In this procedure, an acid derivative (8) in $CH_2Cl_2$ is mixed, at room temperature, with an equimolar amount of the 4-aminopyridine derivative (7). To this solution, an equimolar amount of 1,3-dicyclohexyl-carbodiimide is added. The mixture is stirred about 20 hours, then filtered. The residue is taken up in methylene chloride and filtered again to remove any residual 1,3-dicyclohexyl urea.

Compounds of formula (1) can also be prepared using the procedures illustrated in the following schemes 2 and 3.

Scheme 2

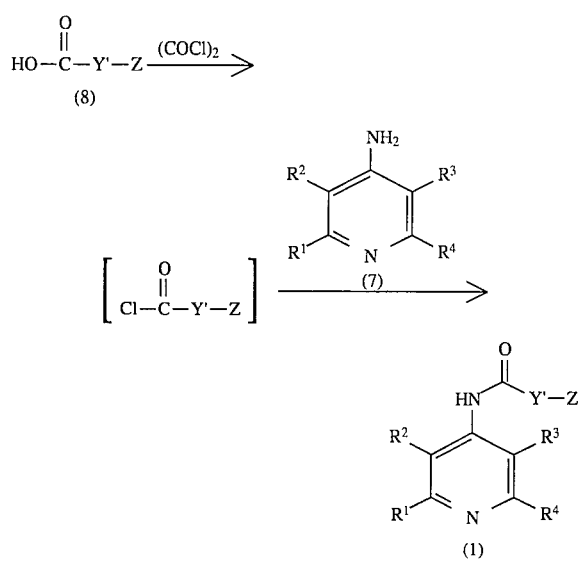

In the procedure illustrated in Scheme 2, a slight excess of oxalyl chloride is added dropwise to a solution of the carboxylic acid (8) in a suitable organic solvent, such as THF, methylene chloride, or xylenes, under nitrogen, at room temperature. The mixture may also include 1–2 equivalents of pyridine or triethylamine. After stirring the mixture for 30 minutes to 2 hours, the amine, in solution in a suitable organic solvent, such as THF, methylene chloride, or xylene, is added dropwise. The mixture is heated to reflux for 8 to 24 hours, then allowed to cool to room temperature and partitioned between 1N sodium hydroxide and ethyl ether. The aqueous phase is extracted with ethyl ether. The combined organics are washed with water and saturated sodium chloride solution, then dried, filtered, and concentrated.

Scheme 3

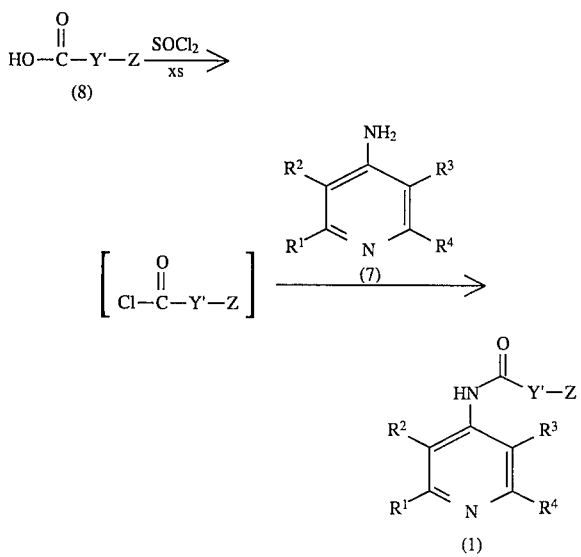

In the procedure illustrated in Scheme 3, an acid derivative (8) is heated to reflux in excess thionyl chloride for about two hours. The excess thionyl chloride is then removed by reducing pressure. To the residue is then added a solution of the aminopyridine (7), and optionally about two equivalents of triethylamine, in a suitable organic solvent, such as acetonitrile, toluene, or xylene. The mixture is heated to reflux for 8 to 24 hours, then allowed to cool to room temperature and partitioned between 1N sodium hydroxide and ethyl ether. The aqueous phase is extracted with ethyl ether. The combined organics are washed with water and saturated sodium chloride solution, then dried, filtered, and concentrated.

Compounds of formula (7) can be prepared using known procedures. For example, the preparation of 2-alkyl-4-amino-3-bromopyridine and 2-alkyl-4-amino-3-chloropyridine derivatives is described in *J. Med. Chem.* vol. 32, pages 1970–77 (1989). *J. Prakt. Chem.*, vol 331, pages 369–374 (1989) describes bromination of aminopicolines, affording other useful starting materials. Compounds of formula (7) can also be made by reduction of the corresponding azides by procedures similar to *J. Prakt, Chem.*, vol 327, pages 521–522 (1985), as illustrated in Preparation 2 hereinafter.

Carboxylic acid derivatives of formula (8) wherein Z is phenyl or substituted phenyl can be prepared using the known procedures illustrated below in Scheme 4. Carboxylic acid derivatives of formula (8) wherein Z is a group of the formula

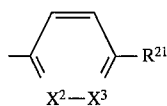

can be prepared using an analogous procedure. Carboxylic acid derivatives of formula (8) wherein z is a group of the formula

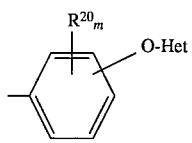

can be prepared by reacting p-hydroxyphenyl acetic acid with the appropriate chloro-substituted heterocyclic compound, as illustrated hereinafter in Preparation 3.

Synthesis of Compounds of Formula (1A) Wherein X is O or S

The compounds of formula (1A) wherein X is O can be made, for example, by condensing a compound of formula (9)

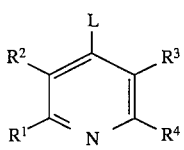

(9)

where $R^1$, $R^2$, $R^3$, and $R^4$ are as defined above for formula (1A) and L is a leaving group such as F, Cl, Br, I, $NO_2$, 1,2,4-triazol-1-yl, $OSi(CH_3)_3$, arylthio, ($C_1$–$C_4$) alkylthio, ($C_1$–$C_4$) alkylsulfonyl, arylsulfonyl, alkoxy, or arylsulfonyl, with an alcohol or phenol of the formula (10):

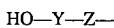 (10)

where Y and Z are as previously defined. The term "aryl" as used in this paragraph refers, for example, to phenyl and substituted phenyl, e.g. 4-nitrophenyl.

The reaction is preferably carried out in the presence of a strong base, such as sodium hydride, in a non-reactive organic solvent, such as DMF, at a temperature in the range of 0° to 25° C.

Compounds wherein X is S are made by the same procedure using analogous mercaptans of formula HS—Y—Z—.

Starting materials of formula (9) are prepared using well known procedures, for example those described in the following European Patent Applications: EPA 326,330 (corresponding to allowed U.S. patent application Ser. No. 07/334,422, filed Apr. 7, 1989), and EPA 326,331 (corresponding to U.S. 5,114,939).

Synthesis of Compounds of Formula (1A) Wherein X is $NR^5$

Compounds of formula (1A) wherein X is $NR^5$ and $R^5$ is H or $C_1$–$C_4$ alkyl can be prepared, for example, by aminating a suitably substituted intermediate of the formula (9). For example, a chloride of formula (9) wherein L is Cl may be reacted with an amine of the formula (11)

$R^{5'}$NH—Y—Z  (11)

where $R^{5'}$ is H or $C_1$–$C_4$ alkyl and Y and Z are as previously defined, at a wide variety of temperatures (20°–180° C.), preferably in the presence of an acid acceptor, such as triethylamine. The reaction may be carried out neat, or in a non-reactive organic solvent.

Alcohols of formula (10) and amines of formula (11) are also readily prepared using conventional procedures, for example the classic chain-lengthening procedure illustrated in the following Scheme 4:

Alternatively, and preferably, amines of formula (1A) are prepared in accordance with the following reaction scheme:

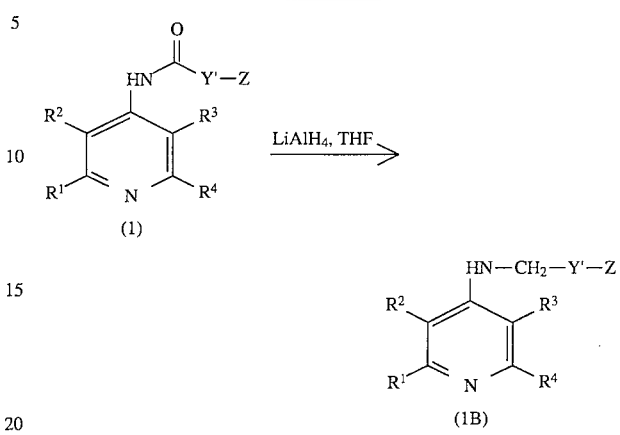

In this procedure the amide of formula (1) is dissolved in THF and added dropwise to a rapidly stirred suspension of lithium aluminum hydride (two fold molar excess) in THF at room temperature. Once the addition is complete, the reaction mixture is heated to reflux. The course of the reaction can be followed by TLC analysis. Once the reaction is complete, the mixture is cooled in an ice bath and quenched by the dropwise addition of saturated ammonium

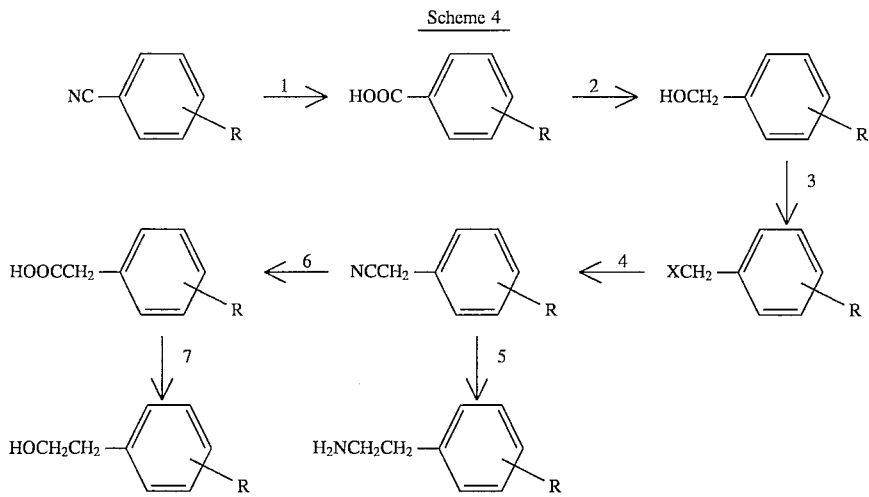

In step 1, KOH hydrolysis of the nitrile produces the corresponding carboxylic acid. In step 2, lithium aluminum hydride reduction of the carboxylic acid produces the alcohol. Alternatively, the alcohol can be obtained by sodium borohydride reduction of the corresponding aldehyde. The halogenation illustrated in step 3 may be, for example, chlorination with thionyl chloride. Treatment of the halide with NaCN in step 4 gives the nitrile. Step 5 is a lithium aluminum hydride reduction of the nitrile using a Lewis acid such as $H_2SO_4$ or $AlCl_3$. In step 6, hydrolysis of the nitrile gives the phenylacetic acid derivative (a compound of formula (8)), which is reduced to the phenethyl alcohol in step 7 using lithium aluminum hydride or other conventional reducing agents.

chloride, followed by 15% sodium hydroxide. The resulting mixture is then filtered and the phases separated. The aqueous phase is extracted with ethyl ether. The combined organics are then dried, filtered, and concentrated.

The N-oxides and salts of compounds of formula (1) and (1A) are obtained in the usual way.

EXAMPLES

The following tables identify compounds of formula (1) and (1A) that were prepared by the processes illustrated in the foregoing schemes. Detailed examples illustrating preparation of exemplary compounds follow the tables.

TABLE I (1)

Structure: Pyridine with 4-NH-C(=O)-Y'Z substituent, R² at 3-position, R³ at 5-position, R¹ at 2-position, R⁴ at 6-position.

| Compound | Y' | Z | R¹ | R² | R³ | R⁴ | MP °C. |
|---|---|---|---|---|---|---|---|
| 1 | CH₂ | –C₆H₄–O(C₂H₅) (para) | H | H | H | H | 104–105 |
| 2 | CH₂ | –C₆H₄–CH(CH₃)₂ (para) | H | H | H | H | oil |
| 3 | CH₂ | –C₆H₄–O(CH₂)₃CH₃ (para) | H | H | H | H | 107 |
| 4 | CH₂ | –C₆H₄–C₆H₅ (biphenyl) | H | H | H | H | 145 |
| 5 | CH₂ | –C₆H₄–(CH₂)₄CH₃ (para) | H | H | H | H | 87 |
| 6 | CH₂ | –C₆H₄–OCH₂CF₃ (para) | H | H | H | H | 120 |
| 7 | CH₂ | –C₆H₄–Cl (ortho) | H | H | H | H | 60 |
| 8 | CH₂ | –C₆H₄–CF₃ (para) | H | H | H | H | 148 |
| 9 | CH₂ | –C₆H₄–O–C₆H₅ (para) | H | H | H | H | |
| 10 | CH₂ | –C₆H₄–O–C₆H₅ (para) | CH₃ | CH₃ | H | H | 92 |
| 11 | CH₂ | –C₆H₄–O–C₆H₄–Cl (para, para'-Cl) | CH₃ | CH₃ | H | H | 148 |
| 12 | CH₂ | –C₆H₄–OCHF₂ (para) | CH₃ | CH₃ | H | H | 146 |

TABLE I-continued (1)

$$\text{structure: pyridine with } R^1, R^2, R^3, R^4 \text{ substituents and HN-C(=O)-Y'Z group}$$

| Compound | Y' | Z | R¹ | R² | R³ | R⁴ | MP °C. |
|---|---|---|---|---|---|---|---|
| 13 | CH₂ | ⌬—O—⌬ | CH₃ | H | H | H | >50 |
| 14 | CH₂ | ⌬—O—⌬ | H | H | Cl | CH₃ | 152 |
| 15 | CH₂ | ⌬—O—⌬ | F | F | F | F | 138 |
| 16 | CH₂ | ⌬—O—⌬ | H | H | H | C₂H₅ | wax |
| 17 | CH₂ | ⌬—O—⌬ | H | Cl | Cl | CH₃ | 139 |
| 18 | CH₂ | ⌬—O—⌬ | H | H | Cl | C₂H₅ | oil |
| 19 | CH₂ | ⌬—OCH₂CF₃ | H | H | Cl | C₂H₅ | 121 |
| 20 | CH₂ | ⌬—t-Bu | H | H | Cl | C₂H₅ | 98 |
| 21 | CH₂ | ⌬—OCH₃ | H | H | Cl | C₂H₅ | 107 |
| 22 | CH₂ | pyridyl—OCH₂CF₃ | H | H | Cl | C₂H₅ | 104 |
| 23 | CH₂ | ⌬—CH(CH₃)₂ | H | H | Cl | C₂H₅ | 90 |
| 24 | CH₂ | ⌬—n-C₅H₁₁ | H | H | Cl | C₂H₅ | 102 |
| 25 | CH₂ | ⌬—n-C₄H₉ | H | H | Cl | C₂H₅ | 92 |

TABLE I-continued (1)

$$\text{structure: pyridine with } R^1, R^2, R^3, R^4 \text{ substituents and } -NH-C(=O)-Y'Z \text{ group at 4-position}$$

| Compound | Y' | Z | $R^1$ | $R^2$ | $R^3$ | $R^4$ | MP °C. |
|---|---|---|---|---|---|---|---|
| 26 | $CH_2$ | -C₆H₄-O-C₆H₅ | H | H | Cl | H | 88 |
| 27 | $CH_2$ | -C₆H₄-O-C₆H₅ | H | H | $CH_3$ | H | 58–61 |
| 28 | $CH_2$ | -C₆H₄-O-C₆H₅ | $CH_3$ | H | $CH_3$ | H | 122 |
| 29 | $CH_2$ | -C₆H₄-O-C₆H₅ (meta) | H | H | Cl | $C_2H_5$ | 63–66 |
| 30 | $CH_2$ | -C₆H₄-O-C₆H₄-Cl | H | H | Cl | $C_2H_5$ | 72–74 |
| 31 | $CH_2$ | -C₆H₄-O-CH(CF$_3$)-CH$_3$ | H | H | Cl | $C_2H_5$ | 75 |
| 32 | $CH_2$ | -C₆H₄-OCH$_2$CF$_2$CHF$_2$ | H | H | Cl | $C_2H_5$ | 102 |
| 33 | $CH_2$ | -C₆H₄-S-C₆H₄-CF$_3$ | H | H | Cl | $C_2H_5$ | 166 |
| 34 | $CH_2$ | -C₆H₄-O-C₆H₄-CF$_3$ | H | H | Cl | $C_2H_5$ | 101.3 |
| 35 | $CH_2$ | -C₆H₄-O-C₆H₅ | $CH_3$ | H | H | $CH_3$ | 56 |
| 36 | $CH_2$ | -C₆H₄-O-C₆H₄-CN | H | H | Cl | $C_2H_5$ | 96 |

TABLE I-continued $$\text{(1)}$$

Structure (1): pyridine with $R^1$ and $R^4$ at 2,6-positions, $R^2$ and $R^3$ at 3,5-positions, and NHC(=O)Y'Z at 4-position.

| Compound | Y' | Z | R¹ | R² | R³ | R⁴ | MP °C. |
|---|---|---|---|---|---|---|---|
| 37 | CH₂ | –C₆H₄–O–C₆H₄–NO₂ | H | H | Cl | C₂H₅ | 120–122 |
| 38 | CH₂ | –C₆H₄–O–C₆H₄–Cl | H | H | Br | C₂H₅ | 73–75 |
| 39 | CH₂ | 2-naphthyl | H | H | Cl | C₂H₅ | 140–141 |
| 40 | CH₂ | –C₆H₃(F)–O–C₆H₄–Cl | H | H | Cl | C₂H₅ | 102–103 |
| 41 | CH₂ | –C₆H₄–OCH₂CF₃ | H | H | H | C₂H₅ | 132–133 |
| 42 | CH₂ | –C₆H₄–t-Bu | H | H | H | C₂H₅ | 105–106 |
| 43 | CH₂ | –C₆H₄–O–C₆H₄–Cl | H | H | H | C₂H₅ | 117–119 |
| 44 | CH₂ | –C₆H₃(F)–O–C₆H₄–CF₃ | H | H | Cl | C₂H₅ | 119–120 |
| 45 | CH₂ | –C₆H₃(F)–OCH₂CF₃ (with additional F) | H | H | Cl | C₂H₅ | 112–114 |
| 46 | CHCH₃ | (CH₂)₇CH₃ | H | H | Cl | C₂H₅ | 52–53 |
| 47 | CH₂ | –C₆H₄–O–C₆H₃(F)–CN | H | H | Cl | C₂H₅ | 117–119 |
| 48 | CH₂ | –C₆H₄–O–C₆H₄–F | H | H | Cl | C₂H₅ | 84–86 |

TABLE I-continued (1) Structure: pyridine with R¹, R², R³, R⁴ substituents and HN-C(=O)-Y'Z group

| Compound | Y' | Z | R¹ | R² | R³ | R⁴ | MP °C. |
|---|---|---|---|---|---|---|---|
| 49 | CH₂ | 4-(4-nitro-2-fluorophenoxy)phenyl | H | H | Cl | C₂H₅ | 139 |
| 50 | CH₂ | 4-(4-methoxyphenoxy)phenyl | H | H | Cl | C₂H₅ | oil |
| 51 | CH₂ | 5-[1-(trifluoromethyl)ethoxy]pyridin-2-yl | H | H | Cl | C₂H₅ | oil |
| 52 | CH₂ | 3-fluoro-4-(4-nitrophenoxy)phenyl | H | H | Cl | C₂H₅ | 152–154 |
| 53 | CH₂ | (CH₂)₅CH₃ | H | H | Cl | C₂H₅ | 58–60 |
| 54 | CH₂ | (CH₂)₇CH₃ | H | H | Cl | C₂H₅ | 63–65 |
| 55 | CH₂ | (CH₂)₉CH₃ | H | H | Cl | C₂H₅ | 78–80 |

TABLE II

(12) Structure: quinoline with R, R³, R⁴ substituents and HN-C(=O)-Y'Z group

| Compound | Y' | Z | R | R³ | R⁴ | MP °C. |
|---|---|---|---|---|---|---|
| 56 | CH₂ | 4-(4-nitrophenoxy)phenyl | 8-F | H | H | 167–169 |
| 57 | CH₂ | 4-(2,2,2-trifluoroethoxy)phenyl | 8-F | H | H | 168–170 |
| 58 | CH₂ | 3-chloro-4-(4-nitrophenoxy)phenyl | 8-F | H | H | glass |
| 59 | CH₂ | 4-(4-chlorophenoxy)phenyl | 8-F | H | H | 169 |

TABLE II-continued (12)

structure: quinoline with R substituent on benzene ring, HN-C(=O)-Y'Z at 4-position, R³ at 3-position, R⁴ at 2-position, N in ring

| Compound | Y' | Z | R | R³ | R⁴ | MP °C. |
|---|---|---|---|---|---|---|
| 60 | CH₂ | -C₆H₄-O-C₆H₄-Cl | H | H | CH₃ | 128–130 |
| 61 | CH₂ | -C₆H₄-O-C₆H₄-Cl | H | H | H | 165–167 |
| 62 | CH₂ | -C₆H₄-O-C₆H₄-CN | 8-F | H | H | 123–125 |
| 63 | CH₂ | -C₆H₄-t-Bu | 8-F | H | H | oil |
| 64 | CH₂ | -C₆H₄-O-C₆H₄-CF₃ | 8-F | H | H | 145–147 |
| 65 | CH₂ | -C₆H₄(F)-O-C₆H₄-CN | 8-F | H | H | 110–112 |

TABLE III (1A)

pyridine with X-Y-Z at 4-position, R² at 3, R³ at 5, R¹ at 2, R⁴ at 6

| Compound | X | Y | Z | R1 | R2 | R3 | R4 | MP °C. |
|---|---|---|---|---|---|---|---|---|
| 1A | O | (CH₂)₂ | -C₆H₄-O-C₆H₄-CF₃ | H | H | H | H | oil |
| 2A | O | (CH₂)₂ | -C₆H₄-OCF₂CF₃ | H | H | H | H | oil |
| 3A | O | (CH₂)₂ | -C₆H₄-O(C₂H₅) | H | H | H | H | oil |
| 4A | O | (CH₂)₂ | -C₆H₄-C(CH₃)₃ | H | H | H | H | oil |

TABLE III-continued $$\underset{R^1}{\overset{R^2}{\diagup}} \underset{N}{\overset{X-Y-Z}{\diagdown}} \underset{R^4}{\overset{R^3}{\diagdown}} \quad (1A)$$

| Compound | X | Y | Z | R1 | R2 | R3 | R4 | MP °C. |
|---|---|---|---|---|---|---|---|---|
| 5A | O | (CH$_2$)$_2$ | –C$_6$H$_4$–C$_6$H$_5$ (4-biphenyl) | H | H | H | H | 55–58 |
| 6A | O | (CH$_2$)$_2$ | –C$_6$H$_4$–OCH$_3$ | H | H | H | H | oil |
| 7A | O | (CH$_2$)$_2$ | –C$_6$H$_4$–Si(CH$_3$)$_3$ | H | H | H | H | | semo

| Compound | X | Y | Z | R1 | R2 | R3 | R4 | MP °C. |
|---|---|---|---|---|---|---|---|---|
| 8A | O | (CH$_2$)$_2$ | –C$_6$H$_4$–OCF$_3$ | H | H | H | H | oil |
| 9A | O | (CH$_2$)$_2$ | –C$_6$H$_4$–OC(CH$_3$)$_3$ | H | H | H | H | oil |
| 10A | O | (CH$_2$)$_2$ | –C$_6$H$_4$–OCH$_2$CF$_3$ | H | H | H | H | oil |
| 11A | NH | (CH$_2$)$_2$ | phenyl | H | H | H | H | 86–88 |
| 12A | NH | (CH$_2$)$_2$ | –C$_6$H$_4$–O(C$_2$H$_5$) | H | H | H | H | 104–105 |
| 13A | NH | (CH$_2$)$_2$ | –C$_6$H$_4$–CH(CH$_3$)$_2$ | H | H | H | H | oil |
| 14A | NH | (CH$_2$)$_2$ | –C$_6$H$_4$–O(CH$_2$)$_3$CH$_3$ | H | H | H | H | 62 |
| 15A | NH | (CH$_2$)$_2$ | –C$_6$H$_4$–C$_6$H$_5$ (4-biphenyl) | H | H | H | H | 140 |
| 16A | NH | (CH$_2$)$_2$ | –C$_6$H$_4$–(CH$_2$)$_4$CH$_3$ | H | H | H | H | oil |
| 17A | NH | (CH$_2$)$_2$ | –C$_6$H$_4$–OCH$_2$CF$_3$ | H | H | H | H | oil |

TABLE III-continued (1A)

$$\text{Structure: Pyridine with } R^1, R^2, R^3, R^4 \text{ substituents and X—Y—Z group at 4-position}$$

| Compound | X | Y | Z | R1 | R2 | R3 | R4 | MP °C. |
|---|---|---|---|---|---|---|---|---|
| 18A | NH | (CH₂)₂ | 2-chlorophenyl | H | H | H | H | oil |
| 19A | NH | (CH₂)₂ | 4-CF₃-phenyl | H | H | H | H | 118–119 |
| 20A | NH | (CH₂)₂ | 4-phenoxyphenyl | H | H | H | H | 108–109 |
| 21A | O | (CH₂)₂ | 2-naphthyl | H | H | H | H | oil |
| 22A | O | (CH₂)₂ | 3-fluoro-4-(OCH₂CF₃)phenyl | H | H | H | H | oil |
| 23A | O | (CH₂)₂ | 2,4-difluorophenyl | H | H | H | H | 35.2 |
| 24A | NH | (CH₂)₂ | 4-phenoxyphenyl | CH₃ | H | H | CH₃ |  |
| 25A | NH | (CH₂)₂ | 4-phenoxyphenyl | CH₃ | CH₃ | H | H |  |
| 26A | NH | (CH₂)₂ | 4-(4-chlorophenoxy)phenyl | CH₃ | CH₃ | H | H | 221 |

The compounds were characterized by 1H NMR. All values were determined in CDCl₃ and recorded as ∂ (ppm).

| Compound No. | Analysis |
|---|---|
| 1A | 3.09 (t, 2H), 4.2 (t, 2H), 6.72–7.59 (m, 10H), 8.38 (m, 2H) |
| 2A | 3.10 (t, 2H), 4.20 (t, 2H), 6.77 (d, 2H), 7.1 7.31 (m, 4H), 8.41 (d, 2H) |
| 3A | 1.40 (t, 3H), 3.03 (t, 2H), 4.02 (q, 2H), 4.15 (t, 2H), 6.78 (d, 2H), 6.84 (d, 2H), 7.16 (d, 2H), 8.39 (d, 2H) |
| 4A | 1.31 (s, 9H), 3.08 (t, 2H), 4.20 (t, 2H), 6.77 (d, 2H), 7.22 (d, 2H), 7.36 (d, 2H), 8.43 (d, 2H) |
| 6A | 2.33 (s, 3H), 3.07 (t, 2H), 4.17 (t, 2H), 6.77 (d, 2H), 7.17 (m, 4H), 8.39 (d, 2H) |
| 7A | 0.27 (s, 9H), 3.11 (t, 2H), 4.22 (t, 2H), 6.79 (d, 2H), 7.27 (d, 2H), 7.49 (d, 2H), 8.41 (d, 2H) |
| 8A | 3.17 (t, 2H), 4.26 (t, 2H), 6.84 (d, 2H), 7.22 (d, 2H), 7.35 (d, 2H), 8.47 (d, 2H) |
| 9A | 1.33 (s, 9H), 3.06 (t, 2H), 4.20 (t, 2H), 6.77–7.17 (m, 6H), 8.41 (d, 2H) |
| 10A | 3.06 (t, 2H), 4.17 (t, 2H), 4.34 (m, 2H), 6.91–6.76 (m, 4H), 7.21 (d, 2H), 8.40 (d, 2H) |
| 13A | 1.24 (d, 6H), 2.2 (1H), 2.8 (q, 2H), 3.4 (m, |

| Compound No. | Analysis |
|---|---|
|  | 3H), 6.46 (t, 2H), 7.13 (d, 2H), 7.16 (d, 2H), 8.16 (t, 2H) |
| 16A | .089 (t, 3H), 1.3–1.6 (m, 6H), 2.58 (t, 2H), 2.88 (t, 2H), 3.41 (m, 1H), 4.3 (bs, 1H), 6.42 (d, 2H), 7.1–7.3 (m, 4H), 8.17 (d, 2H) |
| 17A | 2.87 (t, 2H), 3.39 (td, 2H), 4.33 (q, 2H), 6.41 (d, 2H), 6.90 (d, 2H) 7.15 (d, 2H), 8.16 (d, 2H) |
| 18A | 3.05 (t, 2H), 3.46 (td, 2H), 4.7 (bs, 1H), 6.48 (d, 2H), 7.2–7.4 (m, 4H), 8.15 (d, 2H) |
| 24A | 7.3–6.9 (m, 9H), 6.17 (s, 2H, pyridyl), 4.45 (bs, 1H, NH), 3.41 (td, 2H), 2.89 (t, 2H), 2.39 (s, 6H, CH$_3$'s) |
| 25A | 8.10 (d, 1H, J=6.0Hz, pyridyl H-6), 7.4–6.9 (m, 9H, phenyl), 6.43 (d, 1H, J=6.0Hz, pyridyl H-5), 4.1 (bs, 1H, NH), 3.46 (td, J=6.9, 6.6 Hz, CH$_2$NH), 2.94 (t, 2H, J=7.2Hz, CH$_2$CH$_2$N), 2.48 (s, 3H, CH$_3$), 1.95 (s, 3H, CH$_3$) |

Example 1

N-(4-pyridyl)-4-biphenylacetamide (Compound 4)

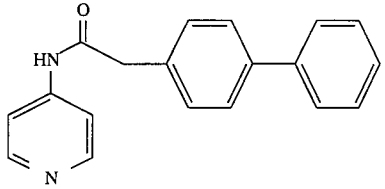

To a solution of 0.941 g (10 mmol) of 4-aminopyridine and 2.123 g of 4-biphenylacetic acid in 50 mL of methylene chloride was added 2.063 g of 1,3-dicyclohexylcarbodiimide. After stirring the mixture at room temperature for about 24 hours, the mixture was filtered and concentrated. The residue was taken up in methylene chloride, filtered and concentrated to give 2.997 g of a flaky, light green solid. This was recrystallized from hexane/ethylacetate and vacuum oven dried to give 2.138 g of a light green solid. Yield 74%. M.P. 145.3° C.

Example 2

N-(3-chloro-2-ethyl-4-pyridyl) (4-isopropylphenyl) acetamide (Compound 23)

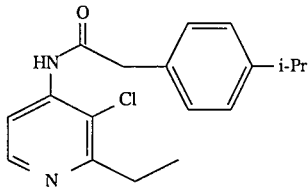

Oxalyl chloride (0.48 mL, 5.50 mmol) was added to a solution of 4-isopropylphenyl acetic acid (0.935 g, 5.25 mmol) in 20 mL of xylene at room temperature. After the mixture was stirred for about 15 minutes, 0.8 mL of pyridine was added. The mixture was stirred for an additional 30 minutes, after which 4-amino-3-chloro-2-ethylpyridine (0.783 g., 5.00 mmol) was added, and the resultant mixture was heated to reflux. After refluxing for about 17 hours, the mixture was allowed to cool to room temperature and partitioned between 1N NaOH (75 mL) and ethyl ether (75 mL). The aqueous phase was extracted with ethyl ether (75 mL). The combined organics were washed with water (1×100 mL), saturated NaCl (1×100 mL), and then dried, filtered, and concentrated to give 1.71 g. of a brown oil. The oil was chromatographed on silica gel, eluting with 80% hexane/20% EtOAc. Isolation of the major product gave 0.391 g. of the desired compound as a solid. M.P. 90° C.

Example 3

N-(3-chloro-2-ethyl-4-pyridyl) (4-((4-(trifluoromethyl)phenyl)oxy)phenyl)acetamide (Compound 34)

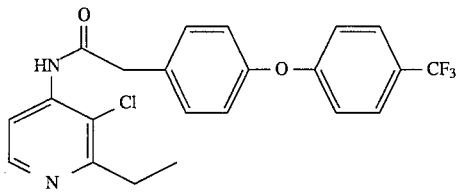

A mixture of (4-((4-(trifluoromethyl)phenyl)oxy)phenyl)acetic acid (1.05 g, 3.5 mmol) and 20 mL of thionyl chloride was heated to reflux. After refluxing two hours, the excess thionyl chloride was removed by reducing pressure. The residue was then treated with a solution of 4-amino-3-chloro-2-ethylpyridine and 1 mL of triethylamine in 20 mL of acetonitrile. The mixture was heated and allowed to reflux for about 24 hours, then cooled to room temperature and partitioned between 1N NaOH (75 mL) and ethyl ether (75 mL). The aqueous phase was extracted with ethyl ether (75 mL). The combined organics were washed with water (1×75 mL), saturated NaCl (1×75 mL), and then dried, filtered, and concentrated to give 1.32 g. of a yellow oil. The was chromatographed on silica gel, eluting with 80% hexane/20% EtOAc. Isolation of the major product gave 0.202 g. of the desired compound as a solid. M.P. 101.3° C.

Preparation 1

4-Azido-8-fluoroquinoline

A mixture of 2.08 g (0.0114 mol) of 4-chloro-8-fluoroquinoline, 1.12 g (0.0172 mol) of sodium azide, and 4.10 g ((0.0127 mol) of tetrabutyl ammonium bromide in 70 mL of dichloromethane and 25 mL of water was refluxed overnight. The layers were then separated and the organic layer was washed once with water, passed through phase separating paper, and concentrated to an oil, which was triturated with ether. The solid was filtered and the filtrate was concentrated to give 2.0 g of the title product.

Preparation 2

4-Amino-8-fluoroquinoline

To a solution at 15°–20° C of 4-azido-8-fluoroquinoline in 12 mL of absolute ethanol was added a portion of 0.57g (0.015 mol) of sodium borohydride. A powerful exotherm with vigorous evolution of gas was observed. The solution was cooled in ice and the remainder of the hydride was added in small portions within five minutes. The ice bath was then is removed. After about two hours, the mixture was poured into about 200 mL of ice water. The precipitate was collected and air dried overnight. Yield 1.35 g. M.P. 184°–186° C.

Example 4

N-(8-fluoro-4-quinolinyl) (4-((4-chlorophenyl)oxy)phenyl)acetamide (Compound 59)

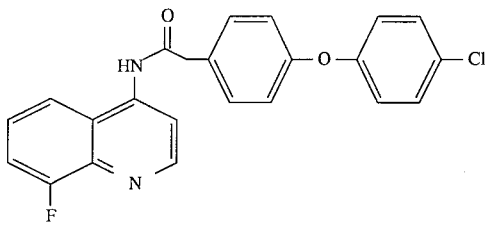

A mixture of 0.63 g (0.0024 mol) of (4-(4chlorophenyl)oxy)phenylacetic acid and excess (10 mL) of thionyl chloride was refluxed for two hours. Excess thionyl chloride was then removed by reducing pressure, the residue was taken up in xylene and 0.39 g (0.0024 mol) of 4-amino-8fluoroquinoline was added. The mixture was refluxed overnight. The xylene was removed by reducing pressure, then the residue was taken up in methylene chloride and the resulting mixture was washed once with water and once with 0.1N sodium hydroxide. The pH of the aqueous layer was adjusted to 7, and product was extracted with ethyl acetate. The methylene chloride and ethyl acetate layers were combined and dried, concentrated to an oil. NMR indicated that the product was a mixture of the starting acid and the desired product. The product was taken up in methylene chloride, washed with base (0.1N sodium hydroxide), dried, and concentrated to an oil. This was chromatographed 100% $CH_2Cl_2 \rightarrow$ 10% $CH_2Cl_2$/EtOAc in 2%/liter increments, and 0.14 g of the title product was collected. This was mixed with hexane and filtered, giving a light brown solid. Yield 0.13 g. M.P. 169° C.

Preparation 3

4-(3-chloro-6-pyridazinyloxy)phenylacetic acid

To a mixture of 0.54 g (0.013 mol, 2.0 equiv) of 60% sodium hydride/mineral oil dispersion in 10 m of dry DMF was added dropwise at room temperature a solution 1.02 g (0.0067 mol) of the phenylacetic acid in 2.3 mL of DMF. After 15–20 minutes, a solid existed which was difficult to stir. The pyridazine (1.0 g, 0.0067 mol) was then added and the mixture was heated at 60°–65° C. for about 2 hours and was allowed to cool. The mixture was poured onto ice water and was adjusted to pH 5 with 2.0N HCl, and the precipitate was collected. This material was triturated under heptane to afford 880 mg of the title product. MP 124°–127° C.

Example 1A

4-[2-[4-[4-(trifluoromethyl)phenoxy]phenyl]ethoxy]pyridine (Compound 1A)

To a suspension of 0.2 g of 60% NaH (as an oil dispersion, 0.005 m) in 5 mL of DMF was added 1.41 g (0.005 m) of 2-[4-[4-(trifluoromethyl)phenoxy]phenyl]ethanol. The mixture was stirred at room temperature for 30 minutes, until hydrogen evolution ceased. To the mixture was then added 0.79 g (0.005 m) of 4-(methylsulfonyl)pyridine, and the mixture was stirred overnight am room temperature. Excess DMF was then removed in vacuo. The resulting material was diluted with water, and the product was extracted into $CH_2Cl_2$. The $CH_2Cl_2$ layer was separated and filtered through phase separating paper, then concentrated. The residue was adsorbed onto silica gel and chromatographed, eluting with $CH_2Cl_2 \rightarrow$ 30% EtOAc/$CH_2Cl_2$. The resulting material was rechromatographed over fine-particle silica gel, eluting with $CH_2Cl_2 \rightarrow$ 50% EtOAc/$CH_2Cl_2$. Yield 0.5 g.

Example 2A

4-[2-[4-(1,1-dimethylethoxy)phenyl]ethoxy]pyridine (Compound 9A)

To a suspension of about one-half gram of 60% NaH (dispersion in oil) in 10 mL of dry DMF was added 1.5 g (0.0077 m) of 2-[4-(1,1-dimethylethoxy)phenyl]ethanol. The mixture was stirred in a warm water bath until hydrogen evolution ceased. After 30–40 minutes, 1 g (0.0064 m) of 4-(methylsulfonyl)pyridine in 5–7 mL of DMF was added. The mixture was stirred at room temperature overnight, then diluted with water. The product was extracted into $CH_2Cl_2$, and the extracts were washed with saturated brine, filtered through phase separating paper, and concentrated in vacuo. The resulting material was azeotroped with xylene to remove excess DMF. This material was adsorbed onto silica gel and chromatographed over silica gel 60 (230–400 mesh) using $CH_2Cl_2 \rightarrow$ 50% EtOAc/$CH_2Cl_2$ to give the title product as an oil. Yield 0.7 g.

Example 3A

4-[2-[4-(2,2,2-trifluoroethoxy)phenyl]ethoxy]pyridine (Compound 10A)

To a suspension of about one gram of 60% NaH (dispersion in oil) in 20 mL of dry DMF was added 5.2 g (0.023 m) of 2-[4-(2,2,2-trifluoroethoxy)phenyl]ethanol. The mixture was stirred at room temperature for 40 minutes, then 3.1 g (0.02 m) of methylsulfonyl pyridine was added. The mixture was stirred at room temperature overnight, then DMF was evaporated in vacuo, and the residue was diluted with water and extracted with $CH_2Cl_2$. The $CH_2Cl_2$ layer was separated, washed with saturated NaCl solution and filtered through phase separating paper. The product was concentrated to yield 6.2 g of crude product, which was adsorbed onto silica gel and chromatographed over silica gel 60 (230–400 mesh) using $CH_2Cl_2 \rightarrow$ 50% EtOAc/$CH_2Cl_2$ to give the title product as an oil. Yield 2.5 g.

Example 4A

N-(2-Phenylethyl)-4-pyridinamine (Compound 11A)

A mixture composed of 2.0 g (0.0176 m) of 4-chloropyridine and 4.3 g (0.0352 m) of phenethylamine was heated under nitrogen to 160°–165° C for one hour. The mixture was then cooled and 200 mL of a 50/50 mixture of ammonium hydroxide in water was added. The product was extracted into $CH_2Cl_2$, which was then concentrated to dryness. The resulting material was purified by HPLC on silica gel, eluting with ethyl acetate to provide 0.560 g of the title product.

Example 5A

N-[2-(4-biphenylyl)ethyl]pyridin-4-amine (Compound 15A)

A solution of 1.495 g (5.2 mmol) of N-(4-pyridyl)-4-biphenyl-acetamide in 30 mL of THF was added dropwise to a rapidly stirred suspension of 0.49 g of lithium aluminum hydride (13 mmol) in 30 mL of THF at room temperature. Once the addition was complete, the mixture was heated to reflux and was refluxed for approximately 17 hours. The mixture was then cooled in an ice bath and quenched by the dropwise addition of 30 mL of saturated ammonium chloride followed by 2 mL of 15% sodium hydroxide. The mixture was filtered and the phases separated. The aqueous phase was extracted with ethyl ether (2×75 mL). The combined organic phases were then dried, filtered, and concentrated to give 1.68 g of a yellow solid. This was chromatographed on silica gel, eluting with 90% $CHCl_3$/10% $CH_3OH$. Removal of solvent left 1.20 g. of a light yellow solid. This was recrystallized from hexane/ethyl acetate and vacuum oven dried to give 0.773 g of a very light yellow solid. M.P. 140.0° C.

Insecticide and Miticide Utility

The compounds of formulas (1) and (1A) show activity against a number of insects and mites. More specifically, the compounds show activity against melon aphid, which is a member of the insect order Homoptera. Other members of the Homoptera include leafhoppers, planthoppers, pear psylla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

The compounds of formulas (1) and (1A) are useful for reducing populations of insects and mites, and are used in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

Some of the above identified compounds were tested for insecticidal, miticidal and nematicidal activity against eight species. Results are reported in the following table, wherein the following abbreviations are used:

ALH refers to aster leafhopper
BAW refers to beet armyworm
CA refers to cotton aphid
NEM refers to peanut rootknot nematode
SCRW refers to southern corn rootworm
TBW refers to tobacco budworm
TSSM refers to two spotted spider mite
GECR refers to German cockroach In conducting evaluations of insecticidal activity, each test compound was formulated as a 400 ppm solution, and this solution was then diluted with water to give lesser concentrations. The 400 ppm solution was prepared by combining 19.2 mL of 0.05% solution of Tween 20 (polyoxyethylene (20) sorbitan monolaurate) in water with a solution of 8 mg of the compound in 0.8 mL of acetone/EtOH (9/1).

Activity against aster leafhopper (*Macrosteles fascifrons*) was tested as follows. The test was run using concentrations of 400 ppm and 50 ppm. One ounce plastic cups containing a cotton wick was sprayed with 0.4 mL of formulated material using a flat-fan nozzle. The excess moisture was allowed to evaporate. Then five to ten carbon dioxide anesthetized adult leafhoppers were added to each cup. The cups were capped and held at room temperature for 24 hours. Percent mortality was then determined. Activity against beet armyworm (*Spodoptera exiqua*) was evaluated as follows. The test is run using concentrations of 400 ppm and 50 ppm. A general purpose lepidoptera artificial diet was diluted to half strength with a 5% non nutritive agar. 8 mL of this diet material was dispensed into one ounce diet cups. One hour prior to treatment, 35 to 40 eggs were dispensed onto the diet surface. The cups were then sprayed with formulated material through a flat-fan nozzle. Treated cups were air dried prior to sealing with plastic caps. The cups were held for 6 days at room temperature. Activity was then rated based on the total number of live and dead larvae, and on the size of live larvae.

Activity against cotton aphid (*Aphis gossypii*) and two spotted spider mite (*Tetranychus urticae*) was evaluated as follows. Golden crookneck squash plants were grown to the expanded cotyledon stage (about 6 to 8 days). The plants were infested with cotton aphids and two spotted spider mites 16 to 24 hours before application of the test material by transfer of infested foliage cut from a stock colony. Immediately prior to spray application of the test material the transfer foliage is removed from the squash plants. The test is run using concentrations of 400 ppm and 50 ppm. The plants are sprayed with test solution using an atomizing sprayer at 17 psi. Both surfaces of the leaves are covered until runoff, and then allowed to dry. Activity of each compound was determined three days after treatment. Activity was rated as a percent based on the mites/aphids present in plants sprayed with solvent alone.

Activity against peanut root knot nematode (*Meloidogyne arenaria*) was evaluated as follows. Five untreated cucumber seeds are placed into the bottom of a clear one ounce cup, 20 g of clean white sand is added, and the cups were sprayed while rotating on a pedestal allowing 1.0 mL of a 400 ppm solution to be deposited on the sand. To each cup was dispensed 2.5 to 3.0 mL of deionized water containing 300 to 500 nematodes. The cups were held for 10 to 12 days in an environmental growth chamber at a temperature of 76° to 85° F. and ambient humidity of 50 to 60%. After 10 to 12 days the cups were evaluated by inverting the cup and observing nematode mortality and feeding damage to the cucumber plants. Activity on Southern corn rootworm (*Diabrotica undecimpuctata howardi* Barber) was evaluated by adding one mL of test solution containing a predetermined concentration of test compound to a cup containing a kernel of corn in 16 g of sterile soil. This produces a soil concentration of 24 ppm. After 1.5 to 2 hours of drying, five 4th instar corn rootworm larvae were added to the individual cups. Mortality was measured at 3–4 days by emptying the cup onto a pan and inspecting the soil for live rootworms.

Activity against tobacco budworm (*Heliothis virescens*) was evaluated as follows. A general purpose lepidoptera artificial diet was diluted to half strength with a 5% non nutritive agar. 8 mL of this diet material was dispensed into each one ounce diet cup. One hour prior to treatment 18 to 20 eggs were dispensed onto the diet surface. The cups were then sprayed with formulated material through a flat-fan nozzle. The test was run using concentrations of 400 ppm and 50 ppm. Treated cups were air dried prior to sealing with plastic caps. The cups were held for 6 days at room temperature. Activity was then rated based on the total number of live and dead larvae, and on the size of live larvae.

Activity against German cockroach (*Blattella germanicus*) was evaluated as follows. 8 mL of alfalfa based green insect diet material was dispensed into a one ounce diet cup. The cups were then sprayed with formulated material through a flat-fan nozzle. The test was run using concentrations of 400 ppm and 50 ppm. Treated cups were air dried for 24 hours and infested with five late third or early fourth instar German cockroaches. The cups were capped and held for ten days in an environmental growth chamber at a temperature of 76°–85° C. Activity was then rated based on the total number of live and dead insects.

| | INSECTICIDE, MITICIDE, AND NEMATICIDE DATA | | | | | | | |
|---|---|---|---|---|---|---|---|---|
| Compound | ALH 400 ppm 50 ppm | BAW 400 ppm 50 ppm | CA 400 ppm 50 ppm | NEM 400 ppm 50 ppm | SCRW 400 ppm 50 ppm | TBW 400 ppm 50 ppm | TSSM 400 ppm 50 ppm | GECR 400 ppm 50 ppm |
| 1 | 100 | 0 | 0 | 0 | 0 | 0 | 0 | 0 |
| | — | — | — | — | | — | — | — |
| 2 | | | | | | | | |
| 3 | | | | | | | | |
| 4 | 0 | 0 | 0 | | 0 | 70 | 0 | 0 |
| | — | — | — | | — | — | — | — |
| 5 | | 0 | 0 | | 0 | 0 | 0 | 0 |
| | | — | — | | | — | — | — |
| 6 | | 0 | 0 | | 0 | 0 | 0 | 0 |
| | | — | — | | | — | — | — |
| 7 | 0 | 0 | 0 | | 0 | 0 | 0 | 0 |
| | — | — | — | | | — | — | — |
| 8 | 0 | 0 | 0 | | 0 | 0 | 0 | 0 |
| | — | — | — | | | — | — | — |
| 9 | 0 | 0 | 0 | | 0 | 60 | 0 | 20 |
| | — | — | — | | | — | — | — |
| 10 | 100 | 100 | 100 | 100 | 0 | 0 | 100 | 60 |
| | 100 | 0 | 100 | 100 | — | 0 | 100 | 0 |
| 11 | 100 | 100 | 100 | 0 | 0 | 100 | 100 | 100 |
| | 100 | 100 | 100 | 0 | — | 100 | 100 | 0 |
| 12 | 100 | 80 | 0 | 0 | 0 | 60 | 0 | 0 |
| | 100 | 0 | 0 | 0 | — | 100 | 100 | 0 |
| 13 | 100 | 0 | 60 | 0 | 0 | 50 | 100 | 0 |
| | 100 | 0 | 0 | 0 | — | 100 | 100 | 0 |
| 14 | 100 | 100 | 100 | 100 | 0 | 100 | 100 | 20 |
| | 100 | 100 | 100 | 0 | — | 100 | 100 | 40 |
| 15 | 0 | 0 | 0 | 60 | 0 | 0 | 0 | 0 |
| | 0 | 0 | 0 | 0 | — | 0 | 0 | 0 |
| 16 | 100 | 100 | 0 | 40 | 0 | 100 | 0 | 0 |
| | 100 | 0 | 0 | — | — | 0 | 0 | 0 |
| 17 | 0 | 0 | 0 | 0 | 0 | 0 | 0 | 0 |
| | 60 | 0 | 0 | 0 | — | 0 | 0 | 0 |
| 18 | 80 | 100 | 100 | 100 | 100 | 100 | 100 | 100 |
| | 80 | 100 | 100 | — | — | 100 | 100 | 40 |
| 19 | 100 | 100 | 100 | 100 | 100 | 100 | 100 | 40 |
| | 100 | 100 | 100 | — | — | 100 | 100 | 40 |
| 20 | 100 | 100 | 100 | 100 | 0 | 100 | 100 | 80 |
| | 100 | 100 | 100 | — | — | 100 | 100 | 0 |
| 21 | 100 | 100 | 100 | 100 | 0 | 100 | 100 | 0 |
| | 40 | 100 | 70 | — | — | 100 | 100 | 0 |
| 22 | 100 | 100 | 100 | 100 | 100 | 100 | 0 | 60 |
| | 100 | 100 | 100 | — | — | 80 | 0 | 0 |
| 23 | 100 | 100 | 100 | 0 | 0 | 100 | 100 | 20 |
| | 100 | 100 | 90 | — | — | 100 | 100 | 0 |
| 24 | 100 | 100 | 100 | 0 | 0 | 100 | 100 | 80 |
| | 100 | 100 | 100 | — | — | 100 | 100 | 40 |
| 25 | 100 | 100 | 100 | 0 | 100 | 100 | 100 | 80 |
| | 100 | 100 | 100 | — | — | 100 | 100 | 20 |
| 26 | 100 | 100 | 100 | 100 | 0 | 80 | 0 | 0 |
| | 100 | 100 | 90 | — | — | 0 | 0 | 0 |
| 27 | 100 | 100 | 100 | 30 | 0 | 0 | 0 | 0 |
| | 100 | 0 | 100 | — | — | 0 | 0 | 0 |
| 28 | 100 | 0 | 0 | 0 | 0 | 0 | 0 | 0 |
| | 100 | 0 | 0 | 0 | — | 0 | 0 | 0 |

-continued

INSECTICIDE, MITICIDE, AND NEMATICIDE DATA

| Compound | ALH 400 ppm 50 ppm | BAW 400 ppm 50 ppm | CA 400 ppm 50 ppm | NEM 400 ppm | SCRW 400 ppm | TBW 400 ppm 50 ppm | TSSM 400 ppm 50 ppm | GECR 400 ppm 50 ppm |
|---|---|---|---|---|---|---|---|---|
| 29 | 100 | 100 | 100 | 0 | 0 | 100 | 100 | 0 |
|    | 100 | 100 | 100 | 0 | — | 100 | 100 | 0 |
| 30 | 100 | 100 | 100 | 100 | 100 | 100 | 100 | 100 |
|    | 100 | 100 | 100 | — | — | 100 | 100 | 60 |
| 31 | 100 | 100 | 100 | 0 | 100 | 100 | 100 | 40 |
|    | 100 | 100 | 100 | — | — | 100 | 100 | 0 |
| 32 | 80 | 100 | 0 | 0 | 100 | 100 | 0 | 0 |
|    | 60 | 100 | 0 | — | — | 100 | 0 | 0 |
| 33 | 100 | 100 | 100 | 0 | 0 | 80 | 100 | 0 |
|    | 100 | 100 | 0 | — | — | 40 | 0 | 20 |
| 34 | 100 | 100 | 100 | 100 | 100 | 100 | 100 | 100 |
|    | 100 | 100 | 100 | — | — | 100 | 100 | 60 |
| 35 | 80 | 0 | 0 | 0 | 0 | 0 | 0 | 20 |
|    | 80 | 0 | 0 | — | — | 0 | 0 | 0 |
| 36 | 100 | 100 | 100 | 100 | 100 | 100 | 100 | 100 |
|    | 100 | 100 | 100 | — | — | 100 | 100 | 100 |
| 37 | 100 | 100 | 100 | 100 | 100 | 100 | 100 | 100 |
|    | 100 | 100 | 100 | — | — | 100 | 100 | 100 |
| 38 | 100 | 100 | 100 | 100 | 100 | 100 | 100 | 100 |
|    | 100 | 100 | 100 | — | — | 100 | 100 | 100 |
| 39 | 100 | 100 | 100 | 100 | 100 | 100 | 100 | 0 |
|    | 100 | 100 | 100 | — | — | 100 | 100 | 0 |
| 40 | 100 | 100 | 100 | 0 | 100 | 100 | 100 | 100 |
|    | 100 | 100 | 100 | — | — | 100 | 100 | 80 |
| 41 | — | — | — | — | — | — | — | — |
|    | — | — | — | — | — | — | — | — |
| 42 | 100 | 0 | 100 | 0 | 0 | 0 | 100 | — |
|    | 100 | 0 | 100 | — | — | 0 | 100 | — |
| 43 | 100 | 100 | 0 | 0 | 0 | 100 | 0 | — |
|    | 100 | 100 | 0 | — | — | 100 | 0 | — |
| 44 | 100 | 100 | 100 | 0 | 100 | 100 | 100 | — |
|    | 100 | 100 | 100 | — | — | 100 | 100 | — |
| 45 | 100 | 100 | 100 | 0 | 100 | 100 | 100 | — |
|    | 100 | 100 | 100 | — | — | 100 | 0 | — |
| 46 | 100 | 100 | 100 | 0 | 0 | 100 | 100 | — |
|    | 100 | 100 | 100 | — | — | 0 | 100 | — |
| 47 | 100 | 100 | 100 | 0 | 0 | 100 | 100 | — |
|    | 100 | 100 | 100 | — | — | 100 | 100 | — |
| 48 | 100 | 100 | 100 | 0 | 0 | 100 | 100 | — |
|    | 100 | 100 | 100 | — | — | 100 | 100 | — |
| 49 | 100 | 100 | 100 | 0 | 0 | 100 | 0 | — |
|    | 100 | 10 | 100 | — | — | 100 | 0 | — |
| 50 | 100 | 100 | 100 | 0 | 100 | 100 | 100 | — |
|    | 100 | 100 | 100 | — | — | 100 | 100 | — |
| 51 | 100 | 100 | 100 | 0 | 100 | 100 | 100 | — |
|    | 100 | 100 | 100 | — | — | 100 | 100 | — |
| 52 | 100 | 100 | 0 | 0 | 0 | 100 | 0 | — |
|    | 100 | 100 | 0 | — | — | 100 | 0 | — |
| 53 | | | | | | | | |
| 54 | | | | | | | | |
| 55 | | | | | | | | |
| 56 | 100 | 100 | 100 | 0 | 0 | 100 | 100 | 60 |
|    | 100 | 100 | 100 | 0 | 0 | 100 | 100 | 0 |
| 57 | 100 | 100 | 100 | 0 | 0 | 100 | 100 | 0 |
|    | 60 | 100 | 100 | — | — | 100 | 90 | 0 |
| 58 | 60 | 100 | 0 | 100 | 0 | 100 | 0 | 0 |
|    | 80 | 100 | 0 | — | — | 100 | 0 | 0 |
| 59 | 100 | 100 | 100 | 100 | 100 | 100 | 100 | 0 |
|    | 100 | 100 | 100 | — | — | 100 | 100 | 0 |
| 60 | 100 | 100 | 100 | 0 | 0 | 60 | 0 | — |
|    | 80 | 100 | 100 | — | — | 0 | 0 | — |
| 61 | 100 | 100 | 100 | | | 100 | 100 | |
|    | 100 | 100 | 100 | | | 0 | 100 | |
| 62 | 100 | 100 | 100 | 100 | | 100 | 100 | |
|    | 100 | 100 | 100 | 0 | | 100 | 100 | |
| 63 | 100 | 100 | 100 | 0 | 0 | 100 | 90 | |
|    | 100 | 70 | 100 | 0 | 0 | 100 | 80 | |
| 64 | 100 | 100 | 100 | 0 | 100 | 100 | 100 | |
|    | 100 | 100 | 100 | 0 | 0 | 100 | 100 | |

Mite-Insect Screen

Some of the above identified compounds were tested for miticidal and insecticidal activity in the following mite/insect screen.

Results are reported in the following table. The following abbreviations are used in the table:

| COMPOUND | CRW RATE PPM | CRW RESULTS % | SAW SM & MA RATE PPM | SAW RESULTS % | SM RESULTS % | MA RESULTS % |
|---|---|---|---|---|---|---|
| 1A  | 12.00 | 0 | 200 | 0  | 0   | 0   |
|     | 24.00 | 0 | 400 | 0  | 80  | 100 |
| 2A  | 12.00 | 0 | 200 | 0  | 90  | 60  |
|     | 24.00 | 0 | 400 | 0  | 0   | 0   |
| 3A  | 12.00 | 0 | 200 | 0  | 0   | 0   |
|     | 24.00 | 0 | 400 | 0  | 0   | 0   |
| 4A  | 12.00 | 0 | 200 | 0  | 90  | 90  |
|     | 24.00 | 0 | 400 | 0  | 80  | 100 |
| 5A  | 12.00 | 0 | 200 | 0  | 100 | 100 |
|     | 24.00 | 0 | 400 | 0  | 0   | 0   |
| 6A  | 12.00 | 0 | 200 | 0  | 0   | 0   |
|     | 24.00 | 0 | 400 | 0  | 0   | 0   |
| 7A  | 12.00 | 0 | 200 | 0  | 50  | 90  |
|     | 24.00 | 0 | 400 | 0  | 80  | 80  |
| 8A  | 12.00 | 0 | 200 | 0  | 100 | 100 |
|     | 24.00 | 0 | 400 | 0  | 90  | 70  |
| 9A  | 12.00 | 0 | 200 | 0  | 100 | 100 |
|     | 24.00 | 0 | 400 | 60 | 100 | 100 |
| 10A | 12.00 | 0 | 200 | 0  | 60  | 90  |
|     | 24.00 | 0 | 400 | 0  | 80  | 50  |
| 12A | 12.00 | 0 | 200 | 0  | 0   | 0   |
|     | 24.00 | 0 | 400 | 0  | 0   | 0   |
| 13A | 12.00 | 0 | 200 | 0  | 0   | 0   |
|     | 24.00 | 0 | 400 | 0  | 0   | 0   |

CRW refers to corn rootworm
SAW refers to Southern armyworm
SM refers to twospotted spider mites
MA refers to melon aphids.

Each test compound was formulated as a 400 ppm solution, and this solution was then diluted with water to give the indicated concentrations. The 400 ppm solution was prepared by combining 19.2 mL of 0.05% solution of Tween 20 (polyoxyethylene (20) sorbitan monolaurate) in water with a solution of 8 mg of the compound in 0.8 mL of acetone/EtOH (9/1).

Twospotted spider mites (*Tetranychus urticae* Koch) and melon aphids (*Aphis gossypii* Glover) are introduced on squash cotyledons and allowed to establish on both leaf surfaces. Other plants in the same treatment pot are left uninfested. The leaves are then sprayed with test solution using an atomizing sprayer at 17 psi. Both surfaces of the leaves are covered until runoff, and then allowed to dry. Activity of a compound is determined 48 hours after treatment. Activity is rated as a percent based on the mites/aphids present in plants sprayed with solvent alone. An uninfested plant is cut after the spraying and drying steps and placed into a Petri dish containing larval southern armyworm (*Spodopetra eridania* Cramer). The larvae are checked after 72 to 96 hours for mortality and for antifeedant activity of the compound. The ratings are based on comparison to results on plants sprayed with solvent alone.

Activity on Southern corn rootworm (*Diabrotica undecimpuctata howardi* Barber) is evaluated by adding one mL of test solution containing a predetermined concentration of test compound to a cup containing a kernel of corn in 16 g of sterile soil. This produces a soil concentration of 24 ppm. After 1.5 to 2 hours of drying, five 4th instar corn rootworm larvae are added to the individual cups. Mortality is measured at 3–4 days by emptying the cup onto a pan and inspecting the soil for live rootworms.

Nematicide Utility

The compounds of the present invention are particularly useful for reducing populations of nematodes. Accordingly, a significant aspect of the invention is a method of inhibiting a nematode population which comprises applying to a locus of a nematode an effective nematode inactivating amount of a compound of formula (1) or (1A). The term "inhibiting a nematode" refers to a decrease in the numbers of living nematodes. The extent of reduction accomplished by a compound depends upon the application rate of the compound, the particular compound used, and the target species. At least a nematode-inactivating amount should be used. The term "nematode-inactivating amount" is used to describe the amount, which is sufficient to cause a measurable reduction in the treated nematode population.

The method is practiced in accordance with standard techniques for the application of nematicides. In general, good nematicidal activity can be expected at rates of 1–10 lbs/acre. The compound can be formulated as described below in the Compositions section. When formulated as dispersions, nematicides are typically applied as aqueous drenches around growing plants or applied incrementally via irrigation systems. When applied as granules, nematicides may be incorporated into the soil before planting, or applied in a band on top of a seed row, or broadcast and then incorporated into the soil, or used as a side dressing to an established crop.

Compounds showing promising activity in the mite insect screen that is described above were tested against the peanut root knot nematode, *Meloidogyne arenaria*, in the peanut root knot nematode assay. In this test a 200 ppm solution of each test compound is prepared by diluting with water the 400 ppm used in the mite insect screen. Three to four cucumber seeds are placed in 16 g of clean white sand, and 1 mL of the 200 ppm solution of test compound is added. This provides a concentration of the compound in the soil of 12 ppm. The cups are allowed to dry one to two hours, and then one mL of a concentrated (50 to 60 per mL) nematode (*Meloidogyne arenaria*) suspension is added to each cup. The cups are incubated for four to seven days. Then 11 mL of deionized water is added to each cup and the cup is gently shaken to rinse the nematodes from the sand. The suspension is poured into a watchglass and observed under a dissecting microscope at 15×–20×. An activity rating is given based on nematode mortality. Aldicarb, carbofuran, and fenamiphos are used as chemical standard compounds. Results are reported in the following table.

| Compound | Rate ppm in sand | Nematode Results % control |
| --- | --- | --- |
| 1A | 12.00 | 0.00 |
| 2A | 12.00 | 100.00 |
| 3A | 12.00 | 100.00 |
| 5A | 12.00 | 0.00 |
| 6A | 12.00 | 100.00 |
| 7A | 12.00 | 0.00 |
| 8A | 12.00 | 100.00 |
| 9A | 12.00 | 100.00 |
| 10A | 12.00 | 100.00 |
| 12A | 24.00 | 0.00 |
| 13A | 24.00 | 0.00 |

Other compounds were tested against the peanut root knot nematode, *Meloidogyne arenaria*, in a similar standardized screening test in which five untreated cucumber seeds are placed into the bottom of a clear on ounce cup, 20 g of clean white sand is added, and the cups are sprayed while rotating on a pedestal allowing 1.0 mL of a 400 ppm solution (as used in the mite insect screen described above) to be deposited on the sand. To each cup is dispensed 2.5 to 3.0 mL of deionized water containing 300 to 500 nematodes. The cups are held for 10 to 12 days in an environmental growth chamber at a temperature of 76° to 85° F. and ambient humidity of 50 to 60%. After 10 to 12 days the cups are evaluated by inverting the cup and observing nematode mortality and feeding damage to the cucumber plants. Results are reported in the following table.

| Compound | Nematode Results % control |
| --- | --- |
| 15A | 0.00 |
| 17A | 0.00 |
| 20A | 100.00 |
| 21A | 0.00 |
| 22A | 0.00 |
| 23A | 0.00 |

Fungicide Utility

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Greenhouse Tests

The following experiments were performed in the laboratory to determine the fungicidal efficacy of the compounds of the invention.

The test compounds were formulated for application by dissolving 50 mg of the compound into 1.25 mi of solvent. The solvent was prepared by mixing 50 ml of "Tween 20" (polyoxyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in following Table | Host |
| --- | --- | --- |
| *Erysiphe graminis tritici* (powdery mildew) | ERYSGT | wheat |
| *Pyricularia ozyzae* (rice blast) | PYRIOR | rice |
| *Puccinia recondita tritici* (leaf rust) | PUCCRT | wheat |
| *Leptosphaeria nodorum* (glume blotch) | LEPTNO | wheat |
| *Plasmopara viticola* (downy mildew) | PLASVI | grape |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

The following table presents the activity of typical compounds of the present invention when evaluated in this experiment. The effectiveness of test compounds in controlling disease was rated using the following scale.

| COMPOUND NUMBER | ERYSGT | PYRIOR | PUCCRT | LEPTNO | PLASVI |
|---|---|---|---|---|---|
| 1 | − | − | − | − | + |
| 2 | ++ | − | − | 0 | 0 |
| 3 | − | − | +++ | − | ++ |
| 4 | + | ++ | − | +++ | |
| 5 | − | − | ++ | − | − |
| 6 | + | + | + | − | + |
| 7 | − | − | + | − | − |
| 8 | + | − | + | −+ | |
| 9 | + | + | ++ | 0 | 0 |
| 10 | ++ | + | +++ | ++ | +++ |
| 11 | +++ | ++ | +++ | ++ | ++ |
| 12 | ++ | + | ++ | − | + |
| 13 | ++ | ++ | +++ | − | ++ |
| 14 | +++ | +++ | +++ | ++ | +++ |
| 15 | − | + | + | + | ++ |
| 16 | +++ | ++ | +++ | ++ | +++ |
| 17 | − | − | − | − | − |
| 18 | +++ | +++ | +++ | ++ | +++ |
| 19 | +++ | +++ | +++ | ++ | +++ |
| 20 | +++ | +++ | +++ | − | +++ |
| 21 | ++ | ++ | ++ | ++ | ++ |
| 22 | ++ | + | ++ | + | +++ |
| 23 | ++ | + | ++ | + | +++ |
| 24 | ++ | + | ++ | + | +++ |
| 25 | + | + | ++ | + | +++ |
| 26 | ++ | ++ | ++ | + | ++ |
| 27 | ++ | + | + | ++ | ++ |
| 28 | ++ | − | ++ | +++ | ++ |
| 29 | +++ | +++ | ++ | + | +++ |
| 30 | +++ | +++ | ++ | +++ | +++ |
| 31 | +++ | ++ | ++ | ++ | ++ |
| 32 | +++ | + | ++ | ++ | ++ |
| 33 | +++ | + | ++ | + | ++ |
| 34 | +++ | ++ | ++ | +++ | +++ |
| 35 | ++ | + | ++ | ++ | ++ |
| 36 | ++ | + | ++ | + | ++ |
| 37 | ++ | + | ++ | ++ | + |
| 38 | ++ | + | ++ | ++ | + |
| 39 | − | − | ++ | + | − |
| 40 | ++ | + | ++ | ++ | ++ |
| 41 | +++ | +++ | ++ | ++ | ++ |
| 42 | ++ | ++ | ++ | ++ | ++ |
| 43 | +++ | ++ | − | +++ | +++ |
| 44 | ++ | ++ | ++ | ++ | − |
| 45 | ++ | + | ++ | ++ | ++ |
| 46 | ++ | + | ++ | ++ | + |
| 47 | ++ | − | ++ | − | ++ |
| 48 | ++ | ++ | ++ | − | ++ |
| 49 | + | − | ++ | + | − |
| 50 | ++ | ++ | ++ | ++ | ++ |
| 51 | ++ | ++ | ++ | ++ | ++ |
| 52 | + | + | ++ | + | − |
| 53 | | | | | |
| 54 | | | | | |
| 55 | | | | | |
| 56 | +++ | ++ | 0 | ++ | +++ |
| 57 | +++ | − | 0 | − | +++ |
| 58 | +++ | + | 0 | + | + |
| 59 | +++ | ++ | 0 | + | +++ |
| 60 | + | − | 0 | − | + |
| 61 | − | − | 0 | − | +++ |
| 62 | + | − | 0 | + | +++ |
| 63 | + | +++ | 0 | ++ | +++ |
| 64 | +++ | + | 0 | ++ | +++ |
| 1A | + | − | + | | |
| 2A | + | − | − | | |
| 3A | − | − | + | | |
| 4A | + | + | + | | |
| 5A | − | − | − | | |
| 6A | − | − | − | | |
| 7A | − | ++ | + | | |
| 8A | + | + | − | | |
| 9A | + | − | − | | |
| 10A | + | + | + | | |
| 11A | − | − | − | | |
| 12A | − | − | − | | |
| 13A | + | − | + | | |

-continued

| COMPOUND NUMBER | ERYSGT | PYRIOR | PUCCRT | LEPTNO | PLASVI |
|---|---|---|---|---|---|
| 14A | + | − | + | | |
| 16A | − | − | − | | |
| 20A | + | ++ | ++ | | |
| 21A | − | − | + | | |
| 22A | + | − | + | | |
| 23A | + | − | − | | |

0 = not tested against specific organism
− = 0–19% control at 400 ppm
+ = 20–89% control at 400 ppm
++ = 90–100% control at 400 ppm
+++ = 90–100% control at 100 ppm

Compositions

The compounds of formula (1) and (1A) are applied in the form of compositions which are important embodiments of the invention, and which comprise a compound of formula (1) or (1A) and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling napthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of formula (1) can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
|---|---|
| Compound of formula (1), or (1A) | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |

| B. 1.5 Emulsifiable Concentrate | |
|---|---|
| Compound of formula (1) or (1A) | 18.50% |
| "TOXIMUL D" | 2.50% |
| "TOXIMUL H" | 2.50% |
| "EXXON 200" | 76.50% |

| C. 1.0 Emulsifiable Concentrate | |
|---|---|
| Compound of formula (1) or (1A) | 12.50% |
| N-methylpyrrolidone | 25.00% |
| "TOXIMUL D" | 2.50% |
| "TOXIMUL H" | 2.50% |
| "EXXON 200" | 57.50% |

| D. 1.0 Aqueous Suspension | |
|---|---|
| Compound of formula (1) or (1A) | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |

| E. 1.0 Aqueous Suspension | |
|---|---|
| Compound of formula (1) or (1A) | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |

| F. 1.0 Aqueous Suspension | |
|---|---|
| Compound of formula (1) or (1A) | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |

| G. Wettable Powder | |
|---|---|
| Compound of formula (1) or (1A) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

| H. Granules | |
|---|---|
| Compound of formula (1) or (1A) | 5.0% |
| propylene glycol | 5.0% |
| Exxon 200 | 5.0% |
| Florex 30/60 granular clay | 85.0% |

We claim:
1. A compound of the formula (1):

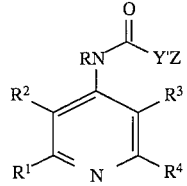

(1)

or an N-oxide or a salt thereof, wherein
R is H or $C_1$–$C_4$ alkyl;
$R^1$, $R^2$, $R^3$, and $R^4$ are one of the following:
  a) $R^3$ and $R^4$ are H, and $R^1$ and $R^2$ are independently halo or $C_1$–$C_4$ alkyl;
  b) one of $R^1$, $R^2$, $R^3$, and $R^4$ is $C_1$–$C_4$ alkyl and the rest are H; or
  c) $R^1$, $R^2$, $R^3$, and $R^4$ are independently H or halo;
Y' is $CH_2$;
Z is phenyl group optionally substituted with one or two groups independently selected from:
  halo,
  phenoxy, optionally substituted with one or two groups selected from halo, CN, $NO_2$, $C_1$–$C_4$-alkoxy, $C_1$–$C_4$ alkyl, or $C_1$–$C_4$ haloalkyl;
  phenyl,
  $C_1$–$C_{12}$ alkyl, straight chain or branched,
  $C_1$–$C_4$ haloalkyl,
  $C_1$–$C_4$ alkoxy;

$C_3$–$C_7$ branched alkoxy,
halo $C_1$–$C_4$ alkoxy,
halo $C_3$–$C_7$ branched alkoxy.

2. A compound of claim 1 wherein Z is a phenyl group substituted with a $C_2$–$C_4$ alkoxy group.

3. A compound of claim 1 wherein Z is a phenyl group substituted with a $C_3$–$C_7$ branched alkoxy group.

4. A compound of claim 1 wherein Z is a phenyl group substituted with a halo $C_2$–$C_4$ alkoxy group.

5. A compound of claim 1 wherein Z is a phenyl group substituted with a group selected from phenoxy and phenoxy substituted with one or two groups selected from halo, CN, $NO_2$, $C_1$–$C_4$-alkoxy, $C_1$–$C_4$ alkyl, $C_1$–$C_4$ haloalkyl.

6. A compound of claim 1 wherein $R^1$ is ($C_1$–$C_4$) alkyl and $R^2$ is halo.

7. A compound of claim 1 wherein $R^1$ is ethyl and $R^2$ is chloro.

8. The compound of claim 1 which is N-(3-chloro-2-ethyl-4-pyridyl)(4-((4-chlorophenyl)oxy)phenyl)acetamide.

9. A method of inhibiting an insect or mite population which comprises applying to the locus of the insect or arachnid an amount of a compound of claim 1 effective to inactivate insects or arachnids.

10. A method of inhibiting a nematode population which comprises applying to the locus of a nematode, an amount of a compound of claim 1 effective to inactivate nematodes.

11. A method of inhibiting plant pathogens which comprises applying an effective amount of a compound of claim 1 to a locus of the pathogen.

12. A pesticide composition which comprises an effective amount of a compound of claim 1 in combination with an agriculturally acceptable carrier.

* * * * *